United States Patent

Konings

Patent Number: 5,603,333
Date of Patent: Feb. 18, 1997

[54] IMPEDANCE CATHETER AND CATHETERIZATION SYSTEM IN WHICH IT IS USED FOR MEASURING THE ELECTRICAL IMPEDANCE IN BLOOD VESSELS

[75] Inventor: Maurits K. Konings, Utrecht, Netherlands

[73] Assignee: Academisch Ziekenhuis Utrecht, Utrecht, Netherlands

[21] Appl. No.: 481,423

[22] PCT Filed: Jan. 5, 1994

[86] PCT No.: PCT/EP94/00019

§ 371 Date: Sep. 6, 1995

§ 102(e) Date: Sep. 6, 1995

[87] PCT Pub. No.: WO94/15529

PCT Pub. Date: Jul. 21, 1994

[30] Foreign Application Priority Data

Jan. 7, 1993 [NL] Netherlands ............................ 9300028

[51] Int. Cl.$^6$ .................................................. G06F 15/42
[52] U.S. Cl. .................................................. 128/734
[58] Field of Search ............................................. 128/734

[56] References Cited

U.S. PATENT DOCUMENTS

| | | | |
|---|---|---|---|
| 3,452,743 | 7/1969 | Rieke | 128/694 |
| 4,840,182 | 6/1989 | Carlson | 128/694 |
| 4,852,580 | 8/1989 | Wood | 128/693 |

FOREIGN PATENT DOCUMENTS

| | | |
|---|---|---|
| 0275617 | 7/1988 | European Pat. Off. |
| 2180072 | 3/1987 | United Kingdom |

OTHER PUBLICATIONS

N. Furuya et al., "Development of multielectrode impedance plethysmography", *Medical and Biological Engineering and Computing*, vol. 24, No. 1, Jan. 1986, pp. 62–70.

*Primary Examiner*—Vincent Millin
*Assistant Examiner*—Robert N. Wieland
*Attorney, Agent, or Firm*—Young & Thompson

[57] ABSTRACT

Method of operating, catheter and catherization system for measuring electrical impedances in blood vessels, within a annular area around the catheter. The catheter contains excitation electrodes, between which the impedance is measured through a potential difference between measuring electrodes present between those electrodes.

Around the catheter a pattern of electrical field lines is created, a so-called counter current field, by varying the amplitude of the currents it being provided that between the measuring electrodes no or hardly any current runs and that at a larger distance of the measuring electrodes the electrical field lines are mainly perpendicular to the longitudinal axis of the catheter. The average impedance of the area to be measured and that of the area outside this will be measured separately. The current intensities then will be chosen such that their relation deviates from the one, at which there is no current between the measuring electrodes—the quenching relation—respectively by adjusting exactly on the quenching relation.

8 Claims, 4 Drawing Sheets

IMPEDANCE CATHETER AND CATHETERIZATION SYSTEM IN WHICH IT IS USED FOR MEASURING THE ELECTRICAL IMPEDANCE IN BLOOD VESSELS

The invention relates to an impedance catheter for measuring electrical impedances in blood vessels, within an annular region around the catheter, the catheter containing excitation electrodes, which are connected to an alternating current source and with measuring electrodes between which a potential difference can be measured.

Measuring that electrical impedance is important for the diagnosis of patients with vascular diseases: by means of the value of the impedances along a vessel route affected by constrictions and/or obstructions, it may be possible in combination with data obtained from X-ray photos or ultrasonography to determine the fat content of the material that causes these constrictions and/or obstructions, without the patient being required to undergo surgery. Actually, the specific electrical impedance of fat is much higher than that of blood, vascular tissue, etcetera.

Atherosclerosis is by far the most occurring form of appearance of coarctation in human beings. In particular this occurs in the abdominal aorta and in the femoral artery with diameters of approximately 5 mm and 3 mm respectively. The importance of information about the fat content in an atherosclerotic lesion is connected with the fact that lesions, rich in fat are less firm of substance than those poor in fat, which makes it easier for them to be torn open, at which a very thrombogenic material is released.

Until now it appeared impossible with the existing diagnostic techniques to distinguish in a reliable manner lesions rich in fat over those poor in fat.

Also adaptation of standard impedance catheterization did not lead to the desired result. Impedance catheterization is a method, at which two excitation electrodes are connected to an alternating current source and the circuit is closed because the current can flow to and fro between the electrodes through the environment in which the catheter is located.

Between de excitation electrodes there are two (or more) measuring electrodes. The voltage difference between those measuring electrodes is a measure for the electrical impedance in the field of current. That this well-known method for measuring impedances did not lead to the intended aim, lies in the fact that one cannot find out whether a change in the impedance takes place near the catheter, in the blood vessel, or farther away, in the tissue next to the blood vessel. Hence conclusions with respect to the blood vessel whether or not being stenosized can not be drawn.

The invention is based on the insight that by using a specific impedance catheter it is possible to determine changes in the impedance in 'inner region' and 'outer region' separately. To that end two current sources are used that are connected to two sets of excitation electrodes in such a way and are actuated with such a relation of the respective current intensities that around the catheter a pattern of electrical field lines is generated, a so-called counter current field, at which through variation of the amplitude of the currents of a set of excitation electrodes as regards the other set it will be possible to see to it that between the measuring electrodes no, or hardly any current runs and at a larger distance of the measuring electrodes the electrical field lines are mainly perpendicular to the longitudinal axis of the catheter and that the average impedance of the area to be measured and that of the area outside this will be measured separately, by choosing the relation of the current intensities in such a way that it deviates from the relation at which there is no current between the measuring electrodes, the quenching relation, and by adjusting that relation exactly to that quenching relation respectively.

The two current sources are connected and actuated, as it were, 'wrongly', which causes the 'counter current field' to come into existence around the catheter. When such a catheter, adjusted in such a way that there is no or hardly any current flowing between the measuring electrodes, passes a deviating impedance in the small area near the catheter, between the measuring electrodes, that will hardly influence the measured potential difference. At such a counter current field, at which the current fields coming from the two current sources, extinguish each other on the spot of the measuring electrodes, the catheter is fit to detect deviating impedances at a larger distance from the catheter. Said extinguishing is realised at a certain relation—the quenching relation—of the current intensity of the two current-sources. When the current intensity adjustment starts to deviate from that quenching relation, the electrical field lines pattern becomes more and more such that near the catheter the electrical field lines run approximately parallel to the longitudinal axis of the catheter, so that the influence of deviating impedances in the area near the catheter, between the measuring electrodes becomes relatively larger. By using both the electrical quenching situation and a current source adjustment deviating therefrom that deviation amounting in particular to more than 5%—it will be possible for each position of the catheter in a blood vessel, to determine from the combined measuring data the average impedance for the area outside the blood vessel and the average impedance of the area within the blood vessel—the relevant area in this matter.

Because by using the above method, the division between inner and outer region has been, provided for in advance, the method is very insensitive to disturbances.

Since the numerical value of the quenching relation, which in a certain situation belongs to the counter current field to be generated, depends on the presence of large deviating impedances near the excitation electrodes, that value can never be exactly predicted. That problem may be solved by adjusting that relation with the help of a feedback mechanism.

An extra switch is needed for this feedback measuring and it is also important that the measuring electrodes are located very near each other. The impedance catheter with which the method, described herein before can be realized thereto shows the characteristic that it contains at least four excitation electrodes that are connected to at least two alternating current sources of which at least two are in counterphase, whose amplitudes can be controlled independent from each other and that it is provided with one or more groups of measuring electrodes, containing per group at least three equidistant electrodes, which as compared to the positioning of the electrodes according to the standard method for measuring this kind of impedances under consideration, are located very close to each other, in such a way that the distance of an arbitrary measuring electrode in a group to a closest other measuring electrode in the same group is the same for all measuring electrodes and smaller than the radius of the blood vessel to be measured, and that no excitation electrode is present between two measuring electrodes. As to the diameter of the blood vessels to be measured: they range from about 3 mm (the femoral artery) to approximately 5 mm (the abdominal aorta).

The invention also covers an impedance catheterization system, containing a catheter according to the invention, it being provided with a preferably digitally controlled switch, with which it may determined between which two measuring electrodes the potential difference is measured.

By applying the methods described, using the impedance catheter and system according to the invention, it will be possible to get a picture of the course of the impedance across the length of the blood vessel to be measured. The catheter is pulled lengthwise through the blood vessel with a speed of preferably not more than 1 cm/sec, each time the impedances being measured in small annular regions located one behind the other within a cylinder around the catheter. Each time when a certain small distance, preferably smaller than the radius of the blood vessel to be measured, has been covered by the catheter, quickly preferably within 10 milliseconds, in a row at least five potential differences are measured: on various pairs of measuring electrodes and at various adjustments of the current sources. From a linear combination of all measuring data thus obtained the impedance in every small annular region around the catheter can be calculated.

Preferably the impedance catheterization system according to the invention is provided with a digitally controlled switching system, with which one can determine which excitation electrode is connected with which pole of which current source.

In a further preferred embodiment the catheterization system according to the invention contains one group of measuring electrodes and is further, in addition to the switch already mentioned, provided with a second switch, with two positions: the counter current position and the parallel position, in the counter current position the two excitation electrodes that are located nearest to the measuring electrodes, being connected to the same current source and in the parallel position being connected to different current sources. In particular such a system contains for instance three measuring electrodes and two current sources and further an electrical device for measuring the potential differences, consisting of one or more 4th class strip guides, signal processors and an AD converter adapter to be installed in a computer, both the operation of the switch that selects two measuring electrodes between which the potential difference is measured, and the operation of the switch with which it is opted for the counter current position or the parallel position, being operated from the same computer, through an DA converter adapter and/or digital I/O adapter.

Good results have been obtained with a distance of the middle measuring electrode to every other measuring electrode of 2 millimeters and on each side of the middle measuring electrode, while at a distance of 29 millimeters and at a distance of 35 millimeters, an excitation electrode is situated.

When applying the method as described, using the catheterization system according to the invention, it is preferred that during the movement of the catheter, each time when a distance equal to the smallest distance between two measuring electrodes again has been covered, within 10 milliseconds, the following activities are performed in a row:

a) determining through arithmetic feedback in particular that current relation between the current sources, to which applies that in the counter current position the potential difference between the first and the second measuring electrode is zero, the measuring electrodes having been numbered onwards, starting with the measuring electrode that is located nearest to the opening where the catheter has been brought into the body;

b) measuring the potential difference between the second and the third measuring electrode in the counter current position and at the same current intensity relation;

c) measuring in the parallel position both the potential difference between the first and the second measuring electrode and the potential difference between the second and the third measuring electrode;

d) adjusting a current intensity relation, which differs more than 5% from the relation as meant sub a) and then measuring both at the parallel position and counter current position both the potential difference between the first and the second measuring electrode and the potential difference between the second and the third measuring electrode.

The invention will be further explained by means of the drawings, in which:

FIG. 1 schematically shows a known impedance catheter, as it is used for instance to determine the ventricular output of the heart;

FIG. 2 shows the electrical field lines pattern, belonging to a catheter as shown in FIG. 1;

FIG. 3 schematically shows blood vessels respectively without and with impedances influencing the potential difference to be measured;

FIG. 4 schematically shows an impedance catheterization system according to the counter current principle;

FIG. 5 schematically shows the system according to FIG. 4, but now in the parallel position;

Figure 1:
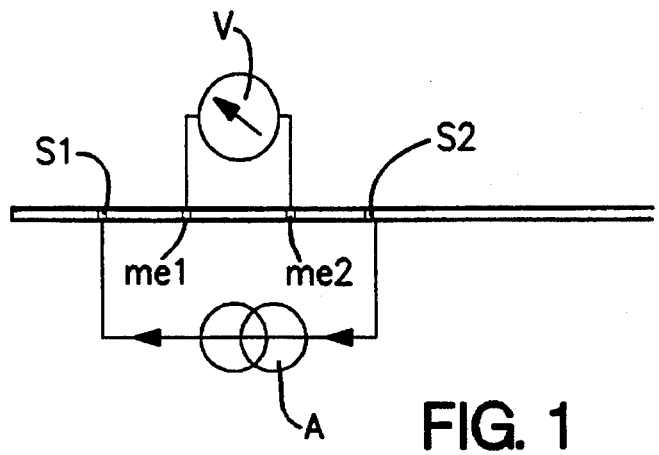

FIG. 1 shows schematically a prevailing impedance catheter (a dipole catheter) with two excitation electrodes ($S_1$ and $S_2$) and two measuring electrodes ($me_1$ and $me_2$). The two excitation electrodes are connected to a current source (A) (alternating current); the circuit is closed because the current can flow from $S_1$ to $S_2$ and vice versa through the environment in which the catheter is located. The voltage difference between the measuring electrodes, as read on the voltmeter (V), is a measure for the electrical impedance in the field of current.

Such an impedance catheter is used to determine the ventricular output of the heart. Since blood conducts electrically better than the myocardium and its surroundings, this current difference will fluctuate during the heart cycle: the larger the diameter (and hence the broader the blood column), the lower the impedance and the current difference will be.

Figure 2:
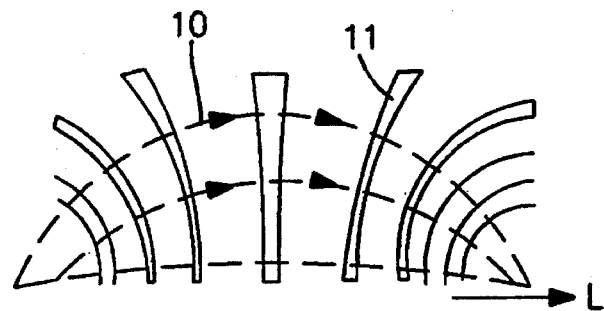

The aim with such a catheter is, to create a current field of which the electrical field lines are as parallel as possible to the longitudinal direction (L) of the catheter—see FIG. 2: dashed lines with arrows [10] are electrical field lines, the continuous black lines [11] are equipotentials—, so that this results in a relation defined as well as possible between the volume of the ventricle and the measured potential differences. For the accuracy of the measurements it then is favourable to place the measuring electrodes not too close to each other. The better the electrical field lines are parallel to the catheter, the more sensitive the potential difference is to changes in the impedance in the environment of the catheter. In view hereof one uses in some cases extra auxiliary current sources, which through extra excitation electrodes (in addition to said $S_1$ and $S_2$) will have the current field run even more homogenously, than is possible with only one current source at a time.

Thus the potential difference measured may give information about the fluctuation of the volume of the ventricle as function of time.

Figure 3:
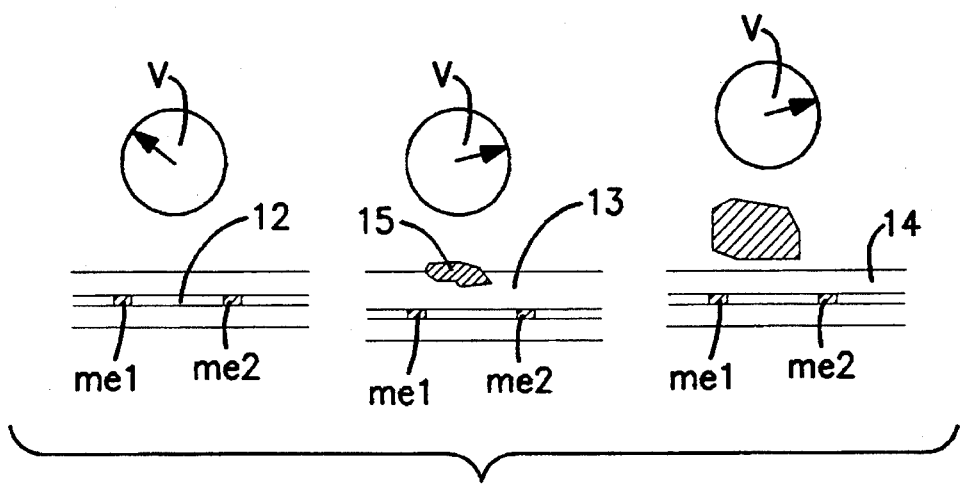

FIG. 3 schematically shows three blood vessel parts 12, 13 and 14, through which a dipole catheter is pulled and of which the impedances are measured. The blood vessel parts 12 and 14 consist of healthy tissue, whereas in part 13 an atherosclerotic lesion (15) of the fat kind is present. The environment of parts 12 and 13 consist of the same material; part 14 runs near a structure with high electrical impedance (for instance bone tissue). The electrical impedance of a fat atherosclerotic lesion is larger than that of blood; this applies, however, also to for instance bone tissue. The potential difference in both part 13 and in part 14 is higher than in part 12. It is hence not possible to conclude from an increased potential difference that a blood vessel shows a fatty lesion: the catheter does not discriminate between the influence of lesion in a blood vessel to the potential difference and that of the impedance outside it.

Figure 4:
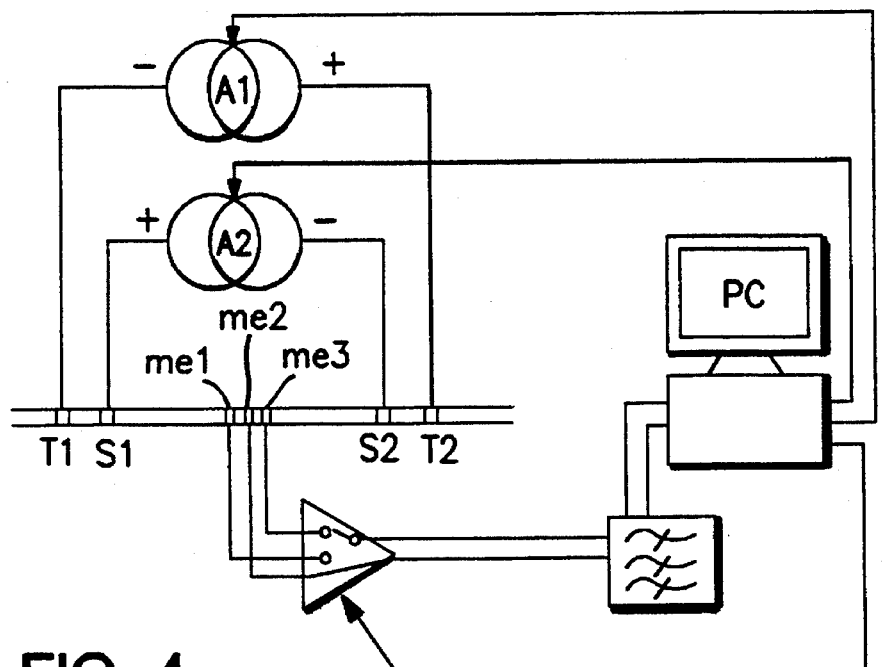

FIG. 4 shows an impedance catheterization system according to the counter current principle. It shows two current sources $A_1$ and $A_2$, four excitation electrodes $S_1$, $S_2$, $T_1$ and $T_2$ and a group of three measuring electrodes $me_1$, $me_2$ and $me_3$. The amplitude of the current of the current sources $A_1$ and $A_2$ can be adjusted; in the drawn case: through a computer and DA converter. The frequencies of the generated alternating currents are the same: for instance 10 kHz and the phase difference between the two alternating currents is 180° (±0.1°). This makes it possible to find for a catheter that is located at a place X (seen in the longitudinal direction of the blood vessel), by varying the amplitude of ($S_1$, $S_2$) and keeping that of ($T_1$, $T_2$) constant, such an adjustment for ($S_1$, $S_2$) that the potential difference, measured between the measuring electrodes $me_1$ and $me_2$ will equal zero: $\phi^T_{12}(x)=0$. This is the earlier mentioned quenching relation: at the spot of the measuring electrodes the two current fields, coming from ($S_1$, $S_2$) and ($T_1$, $T_2$) respectively, extinguish each other: the 'counter current field'— situation.

Then, while the catheter is still lying motionless and the current source adjustments remain the same, it is possible to measure also the potential difference $\phi^T_{23}(x)$ between $me_2$ and $me_3$. Whereas at the known dipole catheter the sensitivity is large in the environment of all electrodes, this is different for the measuring of $\phi^T_{23}(x)$: the area between the measuring electrodes does not show a high sensitivity and the sensitivity decreases less strongly at an increasing radius (seen from the inside towards the outside) as is the case with the dipole catheter.

While the catheter is still lying motionless one may, in order to get a clearly differently shaped sensitivity diagram, equal the amplitude of (S1, S2) to zero (thus a dipole field arises), and then measure $\phi^D_{12}(x)$ and $\phi^D_{23}(x)$. In the sensitivity diagram of the measuring of $\phi^D_{23}$ the area between the measuring electrodes is relatively sensitive, The sensitivity diagrams for the measurements of $\phi^T_{23}$ and $\phi^D_{23}$ have in common that the area around the electrodes S1, S2, T1 and T2 is still very sensitive, which makes the difference around the measuring electrodes relatively insignificant. However, realising that if in general one subtracts two measuring signals $\phi_A - \phi_B$ from each other, the effective sensitivity diagram belonging to the signal $\phi_A - \phi_B$ equals the ('point by point') subtraction of the diagram of $\phi_A$ and that of $\phi_B$, one may determine the diagrams of $\phi^D(x)=\phi hu D_{23}(x)-\phi^D_{12}(x)$ and of $\phi^T(x)=\phi^T_{23}(x)-\phi^T_{12}(x)$.

By measuring in this way $\phi^T(x)$ and $\phi^D(x)$ the desired separation in inner and outer area for a large part has been provided for already: the value of $\phi^T(x)$ is mainly determined by the impedances in the outer area; the value of $\phi^D(x)$ on the contrary is mainly determined by the impedances in the inner region. This makes the result of the final conversion much more reliable.

Figure 6:
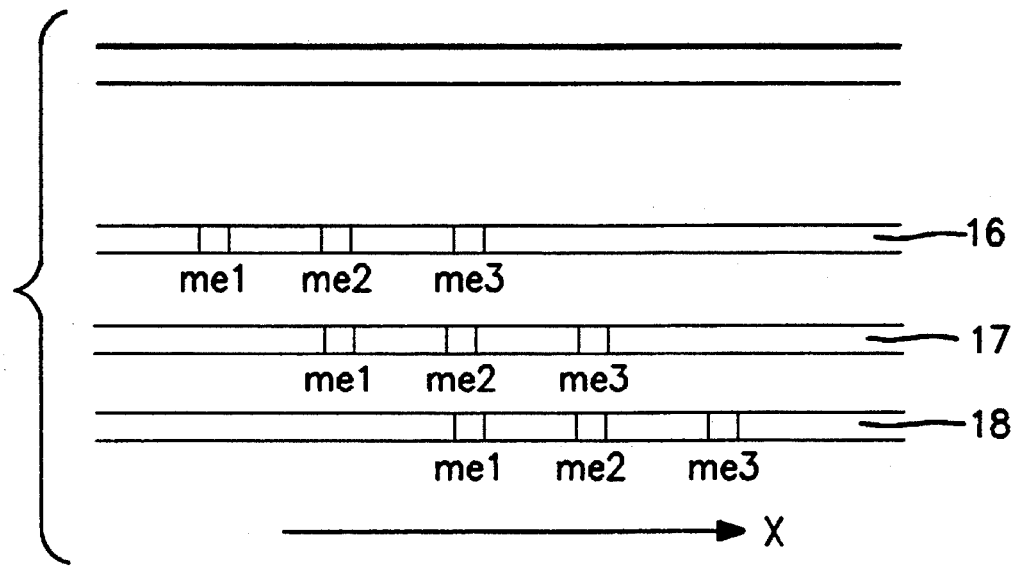
FIG. 6 shows situations where a catheter is pulled through a blood vessel.

FIG. 6 illustrates the situation at which the catheter is moved with a constant speed—along the X axis—in its longitudinal direction: with 16, 17 and 18 three successively occurring situations are shown. At the moment that after departure from situation 16, situation 17 is passed, very quickly $\phi^T(x+dx)$ and $\phi^D(x+dx)$ are measured and stored in the PC memory; meanwhile, during the movement from situation 16 to situation 17, upon approaching situation 17 by means of measurements on the measuring electrode set (me1, me2) the amplitude of (S1, S2) has been adjusted such that $\phi^T_{12}(x+dx)=0$. Upon approaching situation 18 the same happens, so that $\phi^T_{12}(x+dx)=0$. At situation 18 $\phi^T(x+2dx)$ and $\phi^D(x+2dx)$ are measured, etcetera.

This is be continued up to and including the Nth situation, at which N can be chosen as large as desired.

The measuring data have now such a structure that by means of a conversion algorithm all x (at short intervals, smaller than the radius of the blood vessel) $R_{outer}(x)$ and $R_{inner}(x)$ can be calculated herefrom.

Figure 5:
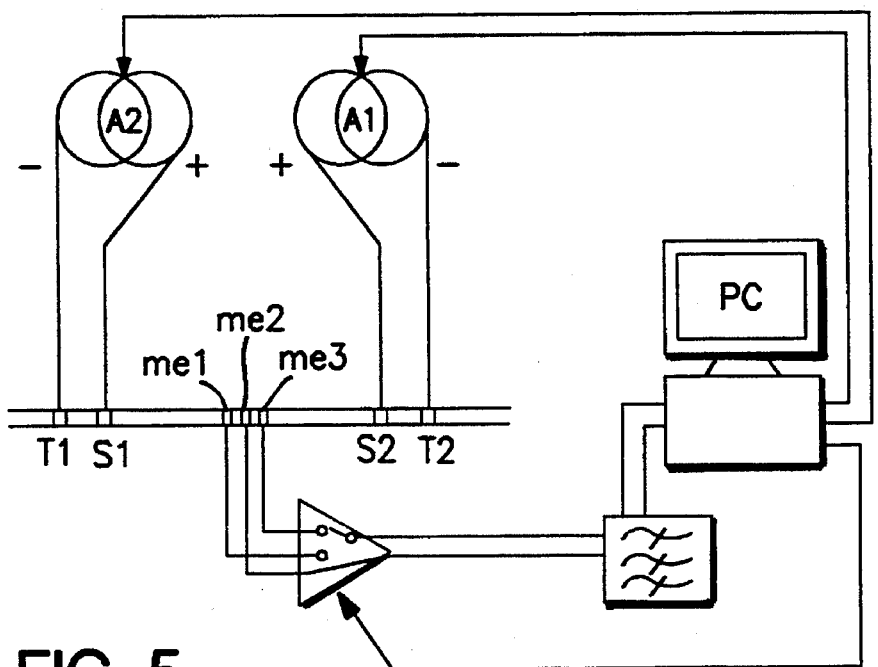

In the counter current catheterization system according to the invention several times feedback is used in addition to the feedback mentioned to $\phi^T_{12}=0$. For this purpose the system contains a second digitally controlled switch system with which the current sources can be connected in two ways to the excitation electrodes; this switch systems accordingly knows two positions:

position 1: the 'Counter current position': switching according to FIG. 4;

position 2: the 'Parallel position': switching according to FIG. 5.

Figure 7:
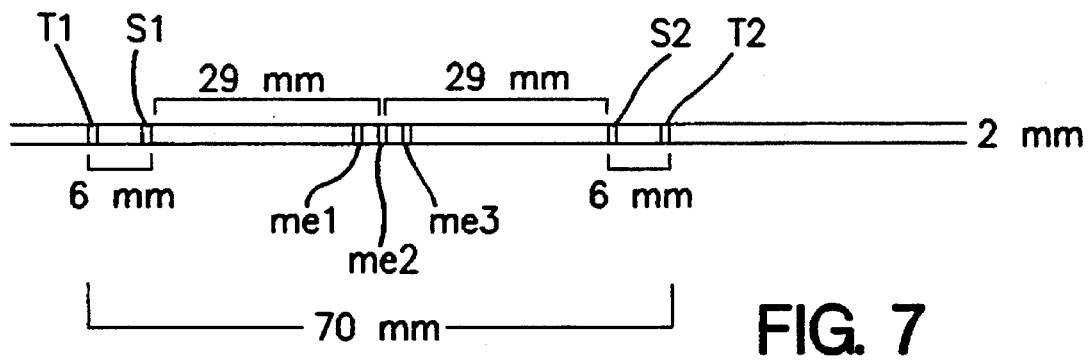
FIG. 7 shows the catheter with indicated therein numerical values with which a good result has been obtained.

In the embodiment example of a catheter shown in FIG. 7, which is used in a counter current catheterization system according to the invention the measurements are indicated.

Figure 8:
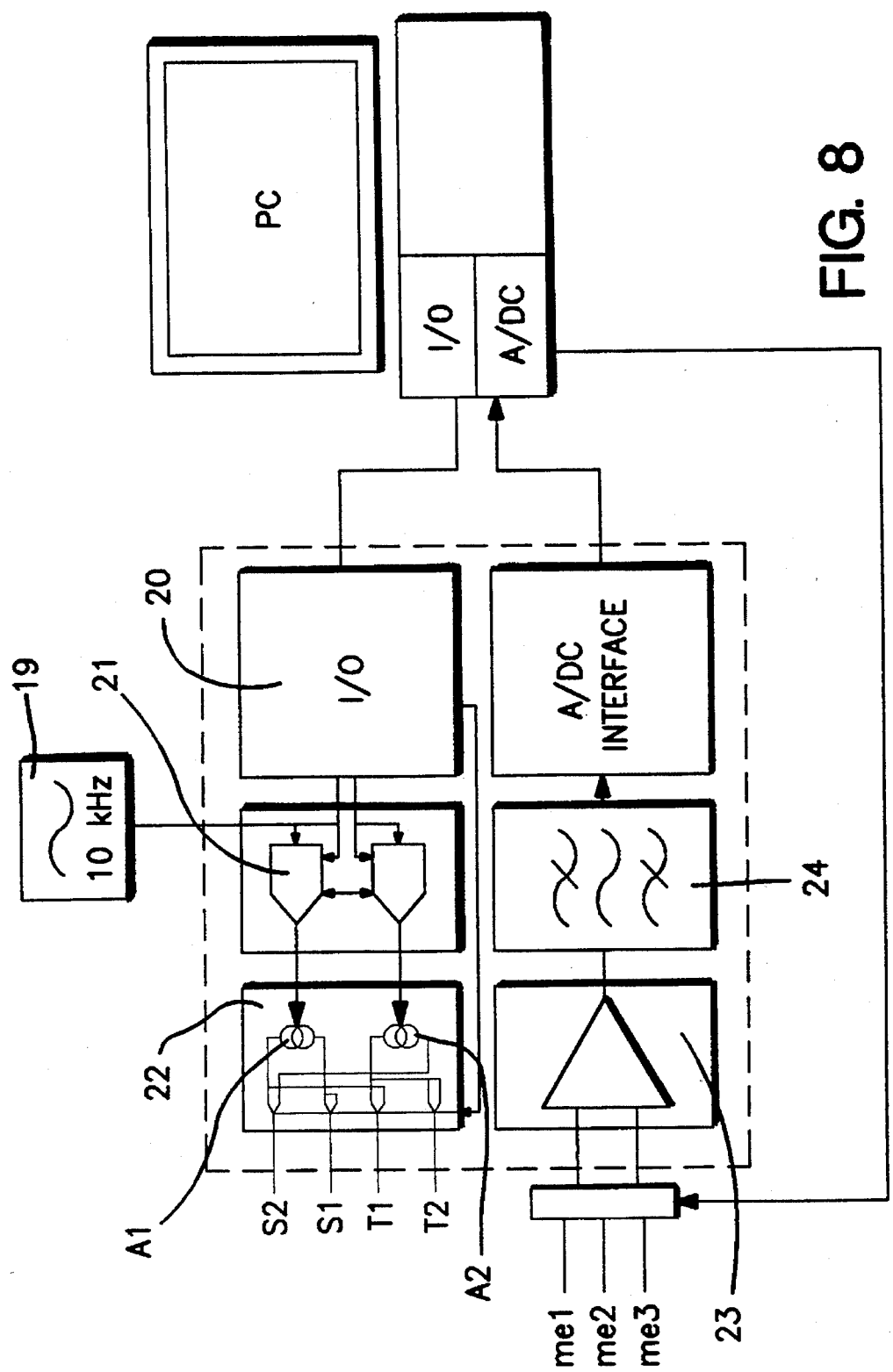
FIG. 8 shows in detail a counter current catheterization system according to the invention.

FIG. 8 shows more detailed an embodiment example of the counter current catheterization system according to the invention, in which [19] is a function generator; [20] is an I/O adapter; [21] are digital attenuators; [22] are current sources with a switch system; [23] is an amplifier with a switch system and [24] is a filter system.

I claim:

1. Impedance catheter for measuring electrical impedances in blood vessels within an annular region around the catheter, containing excitation electrodes, connected to an alternating current source and with measuring electrodes between which a potential difference can be measured, characterised in that it contains at least four excitation electrodes that are connected to at least two alternating current sources of which at least two are in counterphase, whose amplitudes can be controlled independently from each other and that it is provided with one or more groups of measuring electrodes, containing per group at least three equidistant measuring electrodes, which as compared to the positioning of the electrodes according to the standard method for measuring the kind of impedance under consideration are positioned very closely together, such that the distance from one arbitrary measuring electrode in a group, to a nearest other measuring electrode in the same group, for all measuring electrodes is the same and smaller than the radius of the blood vessel to be measured, and that no excitation electrode is present between two measuring electrodes.

2. Impedance catheterization system, containing a catheter according to claim 1, characterised in that it is provided with a digitally controlled switch, with which it may be determined between which measuring electrodes the potential difference is measured.

3. Impedance catheterization system, containing a catheter according to claim 1 characterised in that it is provided with a digitally controlled switch system, with which it may be determined which excitation electrode is connected with which pole of which current source.

4. Impedance catheterization system according to claim 2, that contains one group of measuring electrodes and is provided with a second switch with two positions: the counter current position and the parallel position, in the counter current position the two excitation electrodes that are located closest to the measuring electrodes, being connected to the same current source, and in the parallel position are connected to different current sources.

5. Impedance catheterization system according to claim 4, with three measuring electrodes, with two current sources and with an electrical equipment for measuring potential differences, consisting of one or more 4th class strip guides, signal processors and an AD converter adapter to be installed in a computer, both the operation of the switch that selects two measuring electrodes between which the potential difference is measured, and the operation of the switch with which it is opted for the counter current position or the parallel position, being operated from the same computer, through a DA converter adapter and/or digital I/O adapter.

6. Impedance catheterization system according to claim 5, the distance from the middle measuring electrode to every other measuring electrode amounting to 2 millimeters and on each side of the middle measuring electrode, while at a distance of 29 millimeters and at a distance of 35 millimeters an excitation electrode is situated.

7. Impedance catheterization system, containing a catheter according to claim 2, characterised in that it is provided with a digitally controlled switch system, with which it may be determined which excitation electrode is connected with which pole of which current source.

8. Impedance catheterization system according to claim 3, that contains one group of measuring electrodes and is provided with a second switch with two positions: the counter current position and the parallel position, in the counter current position the two excitation electrodes that are located closest to the measuring electrodes, being connected to the same current source, and in the parallel position are connected to different current sources.

* * * * *